(12) United States Patent
Kim et al.

(10) Patent No.: US 11,833,257 B2
(45) Date of Patent: Dec. 5, 2023

(54) POROUS STRUCTURE AND METHOD FOR MANUFACTURING SAME

(71) Applicant: KOREA INSTITUTE OF INDUSTRIAL TECHNOLOGY, Cheonan-si (KR)

(72) Inventors: Tae Hee Kim, Suwon-si (KR); Jung Nam Im, Suwon-si (KR); Song Jun Doh, Suwon-si (KR); Chaehwa Kim, Seoul (KR); Yoonjin Kim, Yongin-si (KR); Gyu Dong Lee, Ansan-si (KR)

(73) Assignee: KOREA INSTITUTE OF INDUSTRIAL TECHNOLOGY, Cheonan-si (KR)

( * ) Notice: Subject to any disclaimer, the term of this patent is extended or adjusted under 35 U.S.C. 154(b) by 1157 days.

(21) Appl. No.: 15/735,818

(22) PCT Filed: Jun. 10, 2016

(86) PCT No.: PCT/KR2016/006213
§ 371 (c)(1),
(2) Date: Dec. 23, 2019

(87) PCT Pub. No.: WO2016/200218
PCT Pub. Date: Dec. 15, 2016

(65) Prior Publication Data
US 2020/0139001 A1    May 7, 2020

(30) Foreign Application Priority Data
Jun. 12, 2015   (KR) .................. 10-2015-0083576

(51) Int. Cl.
*A61L 15/42*    (2006.01)
*A61F 13/00*    (2006.01)
(Continued)

(52) U.S. Cl.
CPC ...... *A61L 15/425* (2013.01); *A61F 13/00012* (2013.01); *A61F 13/00042* (2013.01);
(Continued)

(58) Field of Classification Search
CPC ...... A61L 15/425; A61L 15/225; A61L 15/44; A61L 2300/102; A61L 2300/418;
(Continued)

(56) References Cited

U.S. PATENT DOCUMENTS 6,344,077 B1    2/2002  Hong
7,019,191 B2    3/2006  Looney et al.
(Continued)

FOREIGN PATENT DOCUMENTS

CN    1872351 A    12/2006
CN    102580134 A    7/2012
(Continued)

OTHER PUBLICATIONS

Chen H, Fan M. Chitosan/Carboxymethyl Cellulose Polyelectrolyte Complex Scaffolds for Pulp Cells Regeneration. Journal of Bioactive and Compatible Polymers. 2007;22(5):475-491. doi:10.1177/0883911507081329 (Year: 2007).*
(Continued)

*Primary Examiner* — K. Boyle
*Assistant Examiner* — Christina H. W. Rosebach
(74) *Attorney, Agent, or Firm* — CANTOR COLBURN LLP

(57) ABSTRACT

Disclosed is a porous structure including water-soluble chitosan; and a carboxymethyl cellulose-based compound, wherein a weight ratio of the water-soluble chitosan and the carboxymethyl cellulose-based compound is from 65:35 to 25:75, and a process for preparing the same.

6 Claims, 17 Drawing Sheets

(51) Int. Cl.
*A61L 15/22* (2006.01)
*A61L 15/44* (2006.01)
*B29C 44/00* (2006.01)
*B29K 105/04* (2006.01)

(52) U.S. Cl.
CPC .. *A61F 13/00063* (2013.01); *A61F 13/00987* (2013.01); *A61L 15/225* (2013.01); *A61L 15/44* (2013.01); *B29C 44/00* (2013.01); *A61L 2300/102* (2013.01); *A61L 2300/418* (2013.01); *A61L 2300/602* (2013.01); *A61L 2400/04* (2013.01); *B29K 2105/04* (2013.01); *C08J 2201/00* (2013.01); *C08J 2301/00* (2013.01); *C08J 2301/02* (2013.01); *C08J 2301/08* (2013.01); *C08J 2305/00* (2013.01); *C08J 2305/08* (2013.01)

(58) Field of Classification Search
CPC ........... A61L 2300/602; A61L 2400/04; A61F 13/00012; A61F 13/00042; A61F 13/00063; A61F 13/00987; B29C 44/00; B29K 2105/04; C08J 2201/00; C08J 2301/00; C08J 2301/02; C08J 2301/08; C08J 2305/00; C08J 2305/08
See application file for complete search history.

(56) References Cited

U.S. PATENT DOCUMENTS

| 9,642,929 | B2 | 5/2017 | Im et al. |
| 2005/0283004 | A1* | 12/2005 | Wei ....................... A61Q 17/04 536/20 |
| 2007/0104769 | A1 | 5/2007 | Feng et al. |
| 2016/0067370 | A1 | 3/2016 | Im et al. |

FOREIGN PATENT DOCUMENTS

| CN | 104693476 A | | 6/2015 |
| CN | 104721222 A | * | 6/2015 |
| EP | 0838491 A2 | | 4/1998 |
| KR | 101998025255 A | | 7/1998 |
| KR | 1020020075539 A | | 10/2002 |
| KR | 1020040086071 A | | 10/2004 |
| KR | 1020060134346 A | | 12/2006 |
| KR | 101318421 B1 | | 10/2013 |
| WO | 9851709 A1 | | 11/1998 |

OTHER PUBLICATIONS

Machine translation of CN 1872351A by He et al. (Year: 2006).*
Sogias, I.A., Khutoryanskiy, V.V. and Williams, A.C. (2010), Exploring the Factors Affecting the Solubility of Chitosan in Water. Macromol. Chem. Phys., 211: 426-433. https://doi.org/10.1002/macp.200900385 (Year: 2010).*
Kubota, N.; Eguchi, Y. Facile Preparation of Water-Soluble N-Acetylated Chitosan and Molecular Weight Dependence of Its Water-Solubility. Polymer Journal, 29, No. 2, pp. 123-127. (Year: 1997).*
Translation of CN 101897990 by Zhang et al. (Year: 2013).*
Lu, Lin et al. "Prevention and treatment of ischemic cardiovascular and cerebrovascular diseases," Jinan: Shandong University Press, Oct. 31, 2010.
Chinese Office Action for CN Application No. 201680034436.X dated Sep. 11, 2020.
Carmen Rosca et al. "Interaction of chitosan with natural or synthetic anionic polyelectrolytes. 1. The chitosan-carboxymethylcellulose complex", Carbohydrate Polymers, Aug. 30, 2005, pp. 35-41, vol. 62.
H. Fukuda et al., "Polyelectrolyte Complexes of Sodium Carboxymethylcellulose With Chitosan", Markromol. Chem., 1979, pp. 1631-1633, vol. 180.
Huangqin Chen et al. "Chitosan/Carboxymethyl Cellulose Polyelectrolyte Complex Scaffolds for Pulp Cells Regeneration", Journal of Bioactive and Compatible Polymers, Sep. 2007, pp. 475-491, vol. 22, No. 5, Sage Publications.
International Search Report dated Oct. 4, 2016 for PCT/KR2016/006213.

* cited by examiner

FIG. 14

| | Absorption time | Before absorption | After absorption |
|---|---|---|---|
| Example 1 | < 1 second | | |
| Example 3 | 13 seconds | | |
| Example 7 | < 1 second | | |
| Comparative Example 1 | 14 seconds | | |
| Comparative Example 2 | 6 seconds | | |
| Comparative Example 3 | > 30 minutes | | |
| Comparative Example 5 | < 1 second | | |
| Comparative Example 6 | < 1 second | | |
| Comparative Example 7 | < 1 second | | |
| Comparative Example 8 | > 30 minutes | | | under a humid environment such as blood or body fluid without additional drug treatment.

POROUS STRUCTURE AND METHOD FOR MANUFACTURING SAME

TECHNICAL FIELD

The present application claims priority to Korean Patent Application No. 10-2015-0083576 filed in the Republic of Korea on Jun. 12, 2015, the disclosures of which are incorporated herein by reference. The present disclosure relates to a porous structure and a process for preparing the same, and more particularly, to a porous structure with outstanding blood absorption capacity, rapid blood coagulation, and improved shape stability and a process for preparing the same.

BACKGROUND ART

In various environments, animals including humans may be injured. This injury often accompanies bleeding. In some cases, injuries and bleeding are not dangerous, and bleeding stops by general blood coagulation activities with no outside help. Unfortunately, in other cases, a considerate amount of bleeding may occur.

Particularly, excessive bleeding endangers human life in an instant and is one of the main leading causes of death, and there are reports that the number of deaths from excessive bleeding in U.S. is over 50,000 each year. The immediate and effective stopping of bleeding can greatly increase the probability of survival, so the use of hemostatic agents in the battlefield, real-life emergency situations, and operating rooms is very necessary.

Humans have devoted themselves for a long time to develop hemostatic agents to stop bleeding quickly, and various formulations for managing bleeding and skin damage occurred by many causes have been developed.

General gauzes or bandages have a hemostatic effect for light bleeding, but their application has limitation in life threatening severe bleeding, and oxidized cellulose-based hemostatic agents have disadvantages because they have somewhat poor blood coagulation capability and adhesion to wound.

Current available hemostatic bandages such as collagen wound dressings or dry fibrin thrombin wound dressings are in limited use for surgical applications, and in particular, in the case of a fast flow of blood such as hemorrhage, they are easily dissolved, which becomes limitation in use. These current available surgical hemostatic bandages are weak and thus are prone to damage caused by bending or loading due to the pressure.

Moreover, collagen-based hemostatic agents are high priced and difficult to preserve, and thrombin- and fibrinogen-containing hemostatic agents have problems with infection risk and hypersensitive reactions during treatment.

Additionally, inorganic-based hemostatic agents such as zeolite have been studied for promoting coagulation in blood, but it was reported that the use of activated zeolite for blood coagulation causes undesirable thermal injury. Inorganic-based hemostatic products with no accompanying fever have been developed, but their blood coagulation capability is not yet good enough to apply to excessive bleeding.

Now, therefore, there are still the need for development of hemostatic agents having improved, better blood coagulation properties and hemostatic effect than earlier hemostatic agents that have been studied.

DISCLOSURE

Technical Problem

The present disclosure is directed to providing a porous structure with outstanding blood absorption capacity, rapid blood coagulation, and superior shape stability.

The present disclosure is further directed to providing a process for preparing the porous structure.

Technical Solution

To achieve the above object, according to an aspect of the present disclosure, there is provided a porous structure including water-soluble chitosan, and a carboxymethyl cellulose-based compound, wherein a weight ratio of the water-soluble chitosan and the carboxymethyl cellulose-based compound is from 65:35 to 25:75.

The porous structure may have an apparent density of from 0.003 to 0.050 g/cm$^3$.

According to another aspect of the present disclosure, there is provided a porous structure including water-soluble chitosan, and a carboxymethyl cellulose-based compound, wherein the carboxymethyl cellulose-based compound is bonded with calcium ions, and a weight ratio of the water-soluble chitosan and the carboxymethyl cellulose-based compound is from 50:50 to 25:75.

A content of the calcium ions may be 0.2 to 10 parts by weight per 100 parts by weight of the water-soluble chitosan and the carboxymethyl cellulose-based compound.

According to another aspect of the present disclosure, there is provided a process for preparing a porous structure, including preparing a composition including water-soluble chitosan, a carboxymethyl cellulose-based compound and water, and freezing and drying the composition, wherein a weight ratio of the water-soluble chitosan and the carboxymethyl cellulose is from 65:35 to 25:75.

The process may further include immersing the porous structure in a solution including a calcium compound and a solvent, and drying.

The process may further include, after the drying, immersing in a mixed solvent of water; and a non-solvent for water-soluble chitosan and a carboxymethyl cellulose-based compound, and drying with heat or hot pressing.

Furthermore, the process may further include gamma radiation after the drying.

Advantageous Effects

The porous structure according to an embodiment of the present disclosure includes a carboxymethyl cellulose-based compound and water-soluble chitosan at the same time, in which the carboxymethyl cellulose-based compound with negative charge of —COO$^-$ in repeating units and the water-soluble chitosan having its surface with —NH$_3^+$ positive charge are held together by ionic bonding to form a complex, thereby providing the porous structure with high shape stability by a freeze-drying method without a process for shape stability such as cross-linking with the addition of a cross-linking agent, or acid treatment to lower the solubility of the carboxymethyl cellulose after making the porous structure or addition of acids to dissolve chitosan.

The porous structure according to an embodiment of the present disclosure has a superior hemostatic function of the water-soluble chitosan, and the outstanding fluid absorption and retention performance and a thickening effect by water absorption of the carboxymethyl cellulose-based compound at the same time, and ionic bonding therebetween solves the conventional problems with a somewhat low absorption rate when chitosan alone is used or poor hemostatic efficiency and shape instability caused by gelation when carboxymethyl cellulose-based compound alone is used, and provides a synergistic effect of the superior fluid absorption properties and hemostatic effect.

Furthermore, because of additionally having bonds with calcium ions, the porous structure according to an embodiment of the present disclosure has the prolonged shape maintenance time even when contacted with blood, contributing to the enhanced shape stability, and releases calcium ions when contacted with blood or body fluid, resulting in further enhanced hemostatic effect.

The porous structure according to an embodiment of the present disclosure can be used as a variety of medical materials including hemostatic agents, adhesion prevention barriers, and wound dressings.

DESCRIPTION OF THE DRAWINGS

The accompanying drawings illustrate preferred embodiments of the present disclosure and, together with the foregoing disclosure, serve to provide further understanding of the technical spirit of the present disclosure. However, the present disclosure is not to be construed as being limited to the drawings.

FIG. 14 is photographic images before and after blood absorption.

MODE FOR CARRYING OUT THE INVENTION

Figure 1:
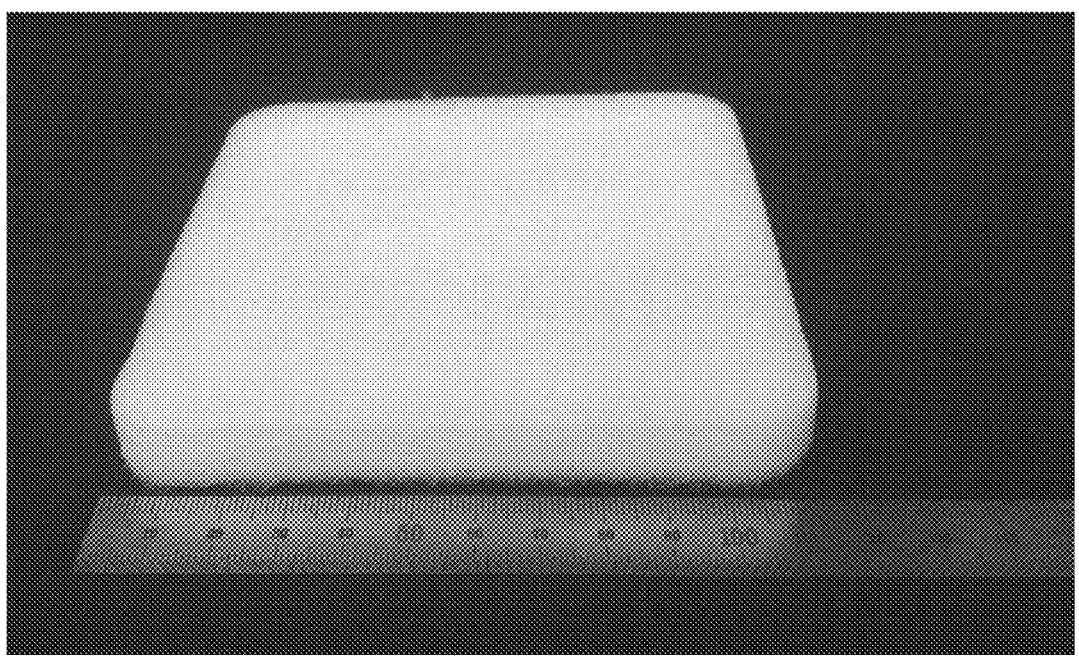
FIG. 1 is a photographic image of a porous structure prepared according to example 1.

Hereinafter, the present disclosure will be described in detail. Prior to the description, it should be understood that the terms or words used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the disclosure described herein are just one most preferred example of the present disclosure, not intended to represent all the technical aspects of the present disclosure, so it should be understood that alternatives, other equivalents and variations would be made thereto at the time the present application is filed.

A porous structure according to an aspect of the present disclosure includes water-soluble chitosan; and a carboxymethyl cellulose-based compound, wherein a weight ratio of the water-soluble chitosan and the carboxymethyl cellulose-based compound is from 65:35 to 25:75.

Chitosan is a compound in deacetylated form of chitin that is a key ingredient of shrimps, crabs, lobsters and cuttlefish, and is being sold in many forms for industrial applications.

The water-soluble chitosan refers to chitosan that dissolves in neutral water, namely, chitosan that dissolves in water without addition of acids for dissolution.

The water-soluble chitosan provides a positively charged surface having strong permeability and a high specific surface area, and the positively charged surface can form a surface that is highly reactive to interaction between red blood cells and platelets. Red blood cell membrane has a negative charge, and is attracted to the positively charged surface of the water-soluble chitosan, and the attracted red blood cell membrane and the water-soluble chitosan are brought into contact and combination with each other, so clots can be formed very quickly. For this reason, the water-soluble chitosan has very good blood coagulation properties, and is linked to bacteria, endotoxin, and microorganisms and exerts an effect on the killing of bacteria, microorganisms, and/or virus formulation.

The water-soluble chitosan includes, but is not limited to, derivatives of water-soluble chitosan lactate, water-soluble chitosan hydrochloride, water-soluble chitosan ascorbate, and low-molecular weight water-soluble chitosan. The derivatives of water-soluble chitosan include, for example, chitosan-PEG and chitosan-bile acid.

According to an embodiment of the present disclosure, the degree of deacetylation of the water-soluble chitosan may be, for example, from 60 to 100%, or from 80 to 100%, and the weight average molecular weight of the water-soluble chitosan may be, for example, from 5,000 to 500,000 g/mol. When the degree of deacetylation and the weight average molecular weight satisfy these ranges, water solubility can be improved, and a hemostatic function and a wound dressing effect can be further enhanced.

The carboxymethyl cellulose-based compound refers to carboxymethyl cellulose or its salt, and the salt includes, but is not limited to, sodium carboxymethyl cellulose, potassium carboxymethyl cellulose, or mixtures thereof.

The carboxymethyl cellulose refers to substitution of a hydroxyl group of glucose that forms cellulose with a carboxymethyl group, and is commonly shortened to CMC. Carboxymethyl cellulose is used in various fields including glues, foods, cosmetics, drug additives and extraction of petroleum, and in particular, is widely used for medical materials because of high biocompatibility.

As a result, carboxymethyl cellulose can be applied for use in adhesion inhibitors, wound dressings, and hemostatic agents. In the case of adhesion inhibitors, it is important to degrade over a predetermined period of time after insertion into the body, while in the case of wound dressings or hemostatic agents, it is important to maintain the shape for a predetermined period of time.

According to an embodiment of the present disclosure, the degree of substitution of carboxymethyl cellulose may be, for example, from 0.4 to 3.0, or from 0.6 to 2.5, or from 0.7 to 1.5. When the degree of substitution satisfies this range, water solubility can be improved.

However, the porous structure of the present disclosure includes the carboxymethyl cellulose-based compound and the water-soluble chitosan at the same time, in which the carboxymethyl cellulose-based compound with negative charge of —COO$^-$ in repeating units and the water-soluble chitosan having its surface with —NH$_3^+$ positive charge are held together by ionic bonding to form a complex. That is, the porous structure with high shape stability can be provided by a freeze-drying method without a process for improving the shape stability such as cross-linking with the addition of a cross-linking agent after making the porous structure, or acid treatment to lower the solubility of carboxymethyl cellulose or addition of acids to dissolve chitosan.

That is, the porous structure according to an embodiment of the present disclosure has both a superior hemostatic function of the water-soluble chitosan and outstanding fluid absorption and retention performance of the carboxymethyl cellulose-based compound, and ionic bonding therebetween solves the conventional problems with a somewhat low absorption rate when chitosan alone is used or reductions in hemostatic function and shape stability caused by gelation when a carboxymethyl cellulose-based compound alone is used, and provides a synergistic effect of the superior fluid absorption properties and hemostatic function.

Furthermore, the hemostatic agent according to an embodiment of the present disclosure can be used as hemostatic agents for filling the body cavities due to having superior physical properties, and ionic bonding between carboxymethyl cellulose and water-soluble chitosan disintegrates when contacted with body fluids, leading to biodegradation over time, which eliminates the need for separate removal after treatment, so it is expected that applicability as hemostatic agents in blood vessels will be high.

A weight ratio of the water-soluble chitosan and the carboxymethyl cellulose-based compound in the porous structure may be from 65:35 to 25:75, particularly from 60:40 to 30:70, and more particularly from 50:50 to 30:70. When the weight ratio satisfies this range, the shape stability is high, the rate of fluid absorption is fast and the hemostatic effect is superior.

Furthermore, the porous structure according to an embodiment of the present disclosure may have the apparent density of from 0.003 to 0.050 g/cm$^3$, particularly from 0.005 to 0.045 g/cm$^3$, and more particularly from 0.010 to 0.040 g/cm$^3$.

The term "apparent density" as used herein refers to density including a pore part in a porous structure having a solid part and the pore part within an object such as powder, particle, fiber, and foam, and can be calculated by dividing the mass of the porous structure by the total volume including the solid part and the pore part.

When the apparent density satisfies this range, the shape stability is high, the rate of fluid absorption is fast, and the fluid retention and hemostatic effect is superior.

A porous structure according to another aspect of the present disclosure includes water-soluble chitosan; and a carboxymethyl cellulose-based compound, wherein the carboxymethyl cellulose-based compound is bonded with calcium ions, and a weight ratio of the water-soluble chitosan and the carboxymethyl cellulose-based compound is from 50:50 to 25:75.

The porous structure is such that the cationic water-soluble chitosan and the anionic carboxymethyl cellulose-based compound are held together by ionic bonding to form a complex as described above, and in this state, calcium ions are bonded with the carboxymethyl cellulose-based compound by additional calcium treatment.

The porous structure further having bonds with calcium ions can have enhanced shape stability due to the prolonged shape maintenance time even when contacted with blood, and have further enhanced hemostatic performance.

In the porous structure having bonds with calcium ions according to an embodiment of the present disclosure, a weight ratio of the water-soluble chitosan and the carboxymethyl cellulose-based compound may be from 50:50 to 25:75, particularly from 50:50 to 30:70, and more particularly from 45:55 to 30:70. When the weight ratio satisfies this range, calcium ion introduction is favorable, the rate of fluid absorption of the hemostatic composition is fast and the hemostatic effect is superior.

According to an embodiment of the present disclosure, the content of calcium ions may be 0.2 to 10 parts by weight, particularly 0.2 to 7 parts by weight, and more particularly 1 to 6 parts by weight per 100 parts by weight of the the water-soluble chitosan and the carboxymethyl cellulose-based compound. When the content of calcium ions satisfies this range, the shape stability of the porous support is enhanced, the hemostatic effect is strengthened, and the rate of fluid absorption is improved.

The porous structure according to an embodiment of the present disclosure may have the blood absorption rate of 15 seconds or less, particularly 10 seconds or less, and more particularly 3 seconds or less.

In this instance, the blood absorption rate is evaluated as the time required for 100 µl of blood to be completely absorbed by a hemostatic porous material of dimensions 1 cm×1 cm×1 cm (width×length×height) after the blood was dripped into the hemostatic porous material.

Furthermore, the porous structure according to an embodiment of the present disclosure may have absorbance of 0.30 or less, particularly 0.25 or less, and more particularly 0.20 or less when evaluating the blood coagulation properties.

In this instance, the evaluation of blood coagulation property was conducted by dripping 100 μl of a mixed solution of blood and an anticoagulant (sodium citrate, 3.8 w/v %) at a volume ratio of 9:1 into a porous structure of dimensions 1 cm×1 cm×1 cm (width×length×height), inducing coagulation in a 37° C. incubator for 10 minutes with the addition of 100 μl of 0.2M $CaCl_2$ aqueous solution, and allowing some of the blood that did not participate in coagulation to be eluted in 12.5 mL of distilled water again. 200 μl of the eluate was taken and measured to determine absorbance [AB] at 540 nm wavelength, 200 μl of distilled water was measured to determine absorbance [AW] at 540 nm wavelength, and calculation was performed by the following equation to obviate the influence of distilled water included in the blood eluate on absorbance.

Absorbance for evaluation of blood coagulation properties=Absorbance of blood eluate [AB]−Absorbance of distilled water [AW]

Furthermore, the porous structure according to an embodiment of the present disclosure may be a product obtained by freeze-drying a composition including the water-soluble chitosan and the carboxymethyl cellulose-based compound. In the case where the porous structure is a freeze-dried product manufactured by a freeze-drying process, advantages are that it is easy to store without a change of ingredients of the porous structure, decomposition or infection by microorganisms can be avoided, and it is easy to add active ingredients, antimicrobials, and hemostatic materials that are sensitive to process temperature.

Furthermore, the porous structure of the present disclosure can be obtained in shape with various outward appearances including a sphere such as a ball, a hexaheron and a tetrahedron, depending on the shape of a frame used to freeze a solution.

Furthermore, the porous structure according to an embodiment of the present disclosure may further include an additive, and the additive may be freely selected according to the required properties, and its examples include bioactive materials, plasticizers, hemostatic materials, antimicrobial materials, cells, enzymes, antigens, and pigments.

According to an embodiment of the present disclosure, a non-toxic plasticizer glycerol may be mixed in optimal amounts to increase the flexibility or adhesive strength of the porous structure, or antimicrobial materials such as silver, silver-based compounds, triclosan, biguanides, and methylene blue may be added to prevent the invasion of microorganisms such as bacteria into the skin.

Furthermore, the bioactive material refers to a material that greatly affects the functions of the body in trace amounts, and includes vitamins, hormones, enzymes, and neurotransmitters, for example, including, but not limited to, human serum albumen, bovine thrombin, human thrombin (h thrombin), rh thrombin, factor VIIa, factor XIII, recombinant factor XIII (rFXIII), thromboxane A2, prostaglandin-2a, epidermal growth factor, platelet-derived growth factor, von Willebrand factor, tumor necrosis factor (TNF), TNF-alpha, transforming growth factor (TGF), TGF-alpha, TGF-beta, insulin-like growth factor, fibroblast growth factor, keratinocyte growth factor, nerve growth factor, penicillin, ampicillin, methicillin, amoxicillin, clavamox, clavulanic acid, amoxicillin, aztreonam, imipenem, streptomycin, kanamycin, tobramycin, gentamicin, vancomycin, clindamycin, erythromycin, polymyxin, bacitracin, amphotericin, nystatin, rifampicin, tetracycline, doxycycline, chloramphenicol and combinations thereof, depending on the nature of wounds or medical conditions of patients. As the hemostatic material, collagen, gelatin, alginate, oxidized cellulose, chitin and chitin derivatives, chitosan derivatives, and calcium chloride may be added.

A process for preparing a porous structure according to another aspect of the present disclosure includes preparing a composition including water-soluble chitosan, a carboxymethyl cellulose-based compound, and water; and freeze-drying the composition, wherein a weight ratio of the water-soluble chitosan and the carboxymethyl cellulose-based compound is from 65:35 to 25:75.

First, a composition including water-soluble chitosan, a carboxymethyl cellulose-based compound, and water is prepared.

The type of the water-soluble chitosan and the carboxymethyl cellulose-based compound is the same as above.

The composition may be obtained by dissolving a carboxymethyl cellulose-based compound in water to prepare an aqueous solution, and subsequently, adding water-soluble chitosan thereto and shaking. Alternatively, on the contrary, the composition may be obtained by shaking while adding a carboxymethyl cellulose-based compound to an aqueous solution of water-soluble chitosan.

Carboxymethyl cellulose-based compound alone or water-soluble chitosan alone may be each obtained in aqueous solution phase, but when they exist together, ionic bonds are formed, failing to be an aqueous solution phase, and through shaking, a composition may be obtained in which an ionic complex of the carboxymethyl cellulose-based compound and the water-soluble chitosan is dispersed or immersed in water.

According to an embodiment of the present disclosure, the concentration of the composition may be from 0.5 to 5.0 w/v %, particularly from 1.0 to 4.0 w/v %, and more particularly from 1.5 to 3.0 w/v %.

In this instance, "w/v %" refers to the unit of concentration representing the weight of solids in the unit volume of the composition, and for example, 1.0 w/v % stands for a composition in which 1 g of solids is dispersed in a dispersion medium to make the total volume of 100 mL.

When the concentration of the composition satisfies this range, it is possible to control various surface structures while maintaining the shape stability, the blood absorption rate is fast and the hemostatic effect is superior.

Subsequently, the composition prepared as above is frozen and dried.

In this instance, the freezing step may be performed at the temperature of, for example 0□ or below, or from −40 to 0□. When the freezing temperature satisfies this range, a resulting porous structure maintains shape stability, and can control the shape and size of pores and the pore distribution to improve the hemostatic properties and have superior fluid absorption properties.

According to an embodiment of the present disclosure, the process may further include the gamma radiation step after the drying step.

The gamma radiation step provides a sterilization for the porous structure, which is directly applied to the skin, without using heat or chemicals. Particularly, treatment by gamma radiation can be performed even in the state where the porous structure is sealed into a final product. The gamma radiation may be performed, for example, at the dose of from 5 to 30 kGy.

According to an embodiment of the present disclosure, a weight ratio of the water-soluble chitosan and the carboxymethyl cellulose-based compound may be from 50:50 to 25:75.

In the case of having this weight ratio, the process may further include immersing the porous structure obtained by the above freeze-drying step in a solution containing a calcium compound and a solvent, followed by drying, to produce the porous structure to which calcium ions are bonded.

The calcium compound includes, but is not limited to, at least one selected from the group consisting of calcium chloride, calcium carbonate, calcium citrate, calcium gluconate, calcium glubionate, calcium hydroxide, and calcium oxalate.

Furthermore, the solvent may be a mixed solvent of water; and a non-solvent for water-soluble chitosan and carboxymethyl cellulose-based compound. The non-solvent for water-soluble chitosan and carboxymethyl cellulose-based compound includes methanol, ethanol, isopropyl alcohol, acetone, methylene chloride, ethyl acetate, and chloroform. For example, the solvent may be a mixed solvent of water and alcohol. The reason that the solvent used in treating with calcium ions is a mixed solvent of water; and a non-solvent for water-soluble chitosan and carboxymethyl cellulose-based compound is to prevent chitosan or carboxymethyl cellulose-based compound from being dissolved by excess water used in the treatment process while introducing calcium ions in aqueous solution phase.

When treating with the solution of calcium compound as described above, calcium ions are bonded with carboxyl group anions of the carboxymethyl cellulose-based compound. In this instance, the process may further include washing to remove unreacted calcium compounds that did not participate in ionic bonding.

According to an embodiment of the present disclosure, the porous structure obtained by the freezing and drying step, which is then immersed in a solution containing a calcium compound and a solvent, may be washed before it undergoes drying. Through the washing step, unreacted calcium compounds or residual solvents may be removed.

According to an embodiment of the present disclosure, the porous structure obtained by freezing and drying, or further treating with calcium as described above may go through further steps of immersing it in a mixed solvent of water; and a non-solvents of water-soluble chitosan and a carboxymethyl cellulose-based compound again, and drying with heat or hot pressing.

As a result, hydrogen bonds between the water-soluble chitosan and hydroxyl groups present in the carboxymethyl cellulose-based compound are formed by water added in the immersing step, and a heatsetting effect is created in the subsequent step of drying with heat or hot pressing, improving the strength of the porous support. When applied to a wound site, the porous structure with improved strength increases in wet strength even after it absorbs blood, thereby increasing convenience in operation and compressing blood vessels more strongly, thus further promoting hemostasis.

Furthermore, according to an embodiment of the present disclosure, gamma radiation may be further performed on the porous structure having undergone the further step of calcium treatment. The gamma radiation step is the same as above.

Further, after being immersed in the mixed solvent of water and a non-solvent, the porous structure may undergo both drying with heat or hot pressing, and gamma radiation. In this instance, the steps may be applied regardless of order, and particularly, the gamma radiation step may be performed in the last step.

Hereinafter, the present disclosure will be described in detail through examples to help understanding. However, the embodiments of the present disclosure may be modified in many different forms, and the scope of the present disclosure should not be construed as being limited to the following examples. The embodiments of the present disclosure are provided to more fully explain the present disclosure to those having ordinary knowledge in the art to which the present disclosure pertains.

Example 1

Sodium Carboxymethyl Cellulose (CMC, Degree of substitution 0.9) was dissolved in distilled water to prepare 2% (w/v) aqueous solution. 200 mL of 2% (w/v) CMC solution was put in a blend mixer, 200 mL of water was added and mixed therewith, and 4 g of water-soluble chitosan (Degree of deacetylation: 87%, Weight average molecular weight 350,000 mol/g) powder was added and strongly shaked. In 2-3 minutes after the addition of water-soluble chitosan, the blend-mixer was strongly shaked again to prepare 2% (w/v) composition in opaque white slurry phase including 50 parts by weight of water-soluble chitosan and 50 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure. The prepared porous structure is shown in FIG. 1. The apparent density of the prepared porous structure was 0.0273 g/cm$^3$.

Example 2

Sodium Carboxymethyl Cellulose (CMC, Degree of substitution 0.9) was dissolved in distilled water to prepare 2% (w/v) aqueous solution. 160 mL of 2% (w/v) CMC solution was put in a blend mixer, 240 mL of water was added and mixed therewith, and 4.8 g of water-soluble chitosan (Degree of deacetylation: 87%, Weight average molecular weight 350,000 mol/g) powder was added and strongly shaked. In 2-3 minutes after the addition of water-soluble chitosan, the blend mixer was strongly shaked again to prepare 2% (w/v) composition in opaque white slurry phase including 60 parts by weight of water-soluble chitosan and 40 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure. The apparent density of the prepared porous structure was 0.0234 g/cm$^3$.

Example 3

Sodium Carboxymethyl Cellulose (CMC, Degree of substitution 0.9) was dissolved in distilled water to prepare 2% (w/v) aqueous solution. 280 mL of 2% (w/v) CMC solution was put in a blend mixer, 120 mL of water was added and mixed therewith, and 2.4 g of water-soluble chitosan (Degree of deacetylation: 87%, Weight average molecular weight 350,000 mol/g) powder was added and strongly shaked. In 2-3 minutes after the addition of water-soluble chitosan, the blend mixer was strongly shaked again to prepare 2% (w/v) composition in opaque white slurry phase including 30 parts by weight of water-soluble chitosan and 70 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure. The apparent density of the prepared porous structure was 0.0230 g/cm$^3$.

Example 4

Sodium Carboxymethyl Cellulose (CMC, Degree of substitution 0.9) was dissolved in distilled water to prepare 2% (w/v) aqueous solution. 100 mL of 2% (w/v) CMC solution was put in a blend mixer, 300 mL of water was added and mixed therewith, and 2.0 g of water-soluble chitosan (Degree of deacetylation: 87%, Weight average molecular weight 350,000 mol/g) powder was added and strongly shaked. In 2-3 minutes after the addition of water-soluble chitosan was added, the blend mixer was strongly shaked again to prepare 1% (w/v) composition in opaque white slurry phase including 50 parts by weight of water-soluble chitosan and 50 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure. The apparent density of the prepared porous structure was 0.0199 g/cm$^3$.

Example 5

Sodium Carboxymethyl Cellulose (CMC, Degree of substitution 0.9) was dissolved in distilled water to prepare 2% (w/v) aqueous solution. 150 mL of 2% (w/v) CMC solution was put in a blend mixer, 250 mL of water was added and mixed therewith, and 3.0 g of water-soluble chitosan (Degree of deacetylation: 87%, Weight average molecular weight 350,000) powder was added and strongly shaked. In 2-3 minutes after the addition of water-soluble chitosan, the blend mixer was strongly shaked again to prepare 1.5% (w/v) composition in opaque white slurry phase including 50 parts by weight of water-soluble chitosan and 50 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure. The apparent density of the prepared porous structure was 0.0270 g/cm$^3$.

Example 6

Sodium Carboxymethyl Cellulose (CMC, Degree of substitution 0.9) was dissolved in distilled water to prepare 2% (w/v) aqueous solution. 250 mL of 2% (w/v) CMC solution was put in a blend mixer, 150 mL of water was added and mixed therewith, and 5.0 g of water-soluble chitosan (Degree of deacetylation: 87%, Weight average molecular weight 350,000 g/mol) powder was added and strongly shaked. In 2-3 minutes after the addition of water-soluble chitosan was added, the blend mixer was strongly shaked again to prepare 2.5% (w/v) composition in opaque white slurry phase including 50 parts by weight of water-soluble chitosan and 50 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure. The apparent density of the prepared porous structure was 0.0375 g/cm$^3$.

Example 7

0.2 g of the porous structure (a 30:70 weight ratio of water-soluble chitosan and sodium carboxymethyl cellulose) prepared in example 3 was immersed in 200 mL of 0.05M solution of $CaCl_2$ in a mixed solvent of ethanol and water at a volume ratio of 8:2 and then shaked at room temperature for 1 hour. After washing in a mixed solution of ethanol and water at a volume ratio of 8:2 twice, and washing in methanol one more time, drying at 50° C. for 90 minutes using a convection oven was performed to prepare a porous structure further including calcium ions.

Example 8

A porous structure further including calcium ions was prepared by the same method as example 7 except the porous structure (a 50:50 weight ratio of water-soluble chitosan and sodium carboxymethyl cellulose) prepared in example 1 was used.

Comparative Example 1

Water-soluble chitosan (Degree of deacetylation: 87%, Weight average molecular weight 350,000 g/mol) powder was dissolved in distilled water to prepare 2% (w/v) aqueous solution. The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure.

Comparative Example 2

Sodium Carboxymethyl Cellulose (CMC, Degree of substitution 0.9) was dissolved in distilled water to prepare 2% (w/v) aqueous solution. 120 mL of 2% (w/v) CMC solution was put in a blend mixer, 280 mL of water was added and mixed therewith, and 5.6 g of water-soluble chitosan (Degree of deacetylation: 87%, Weight average molecular weight 350,000 g/mol) powder was added and strongly shaked. In 2-3 minutes after the addition of water-soluble chitosan was added, the blend mixer was strongly shaked again to prepare 2% (w/v) composition in opaque white slurry phase including 70 parts by weight of water-soluble chitosan and 30 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60□ to prepare a foam-type porous structure.

Comparative Example 3

Sodium Carboxymethyl Cellulose (CMC, Degree of substitution 0.9) was dissolved in distilled water to prepare 2% (w/v) aqueous solution. The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure.

Comparative Example 4

Sodium Carboxymethyl Cellulose (CMC, Degree of substitution 0.9) was dissolved in distilled water to prepare 2% (w/v) aqueous solution. 320 mL of 2% (w/v) CMC solution was put in a blend mixer, 80 mL of water was added and mixed therewith, and 1.6 g of water-soluble chitosan (Degree of deacetylation: 87%, Weight average molecular weight 350,000 g/mol) powder was added and strongly shaked. In 2-3 minutes after the addition of water-soluble chitosan, the blend mixer was strongly shaked again to prepare 2% (w/v) composition in opaque white slurry phase including 20 parts by weight of water-soluble chitosan and 80 parts by weight of sodium carboxymethyl cellulose.

The prepared solution was poured into a polystyrene square petri dish of 125 mm×125 mm×20 mm, frozen at 0° C. for 4 hours and at −15° C. for 24 hours, and vacuum-dried at 60° C. to prepare a foam-type porous structure.

Experimental Example

Evaluation of Fluid Absorption and Retention

In the case of hemostatic dressings that need to stop bleeding fast and absorb a large amount of blood, superior fluid absorption properties for liquid such as blood are required. Furthermore, if blood does not seep through the porous structure and is retained within the porous structure even after certain compression, handling is easy and blood coagulation involving factors accumulated in the porous structure can efficiently help blood coagulation.

The weight (weight before fluid absorption) of the porous structures prepared in examples 1 and 3 and comparative examples 1 to 3 was measured, and after immersing in 0.9% saline solution of 25☐ for 10 minutes, the weight after fluid absorption was measured, fluid absorption was calculated by the following equation, and its results are shown in Table 1.

Fluid absorption (g/g)=[Weight(g) after fluid absorption−Weight(g) before fluid absorption]/[Weight(g) before fluid absorption]

The weight (weight before fluid absorption) of the porous structures prepared in examples 1 and 3 and comparative examples 1 to 3 was measured, and after immersing in 0.9% saline solution of 25☐ for 10 minutes, the pressure of 40 mmHg was applied to the absorbed porous structure for 1 minute, the weight (weight after compression) of the porous structure was measured, fluid retention was calculated by the following equation, and its results are shown in Table 1.

Fluid retention (g/g)=[Weight(g) after compression−Weight(g) before fluid absorption]/[Weight(g) before fluid absorption].

TABLE 1

|  | Fluid absorption (g/g) | Fluid retention (g/g) |
| --- | --- | --- |
| Example 1 | 16 | 10 |
| Example 3 | 65 | 41 |
| Comparative example 1 | Impossible to meausre | Impossible to meausre |
| Comparative example 2 | Impossible to meausre | Impossible to meausre |
| Comparative example 3 | 20 | Impossible to meausre |

Referring to Table 1, in the case of examples 1 and 3, fluid absorption was good enough to absorb an amount of 0.9% saline solution at least 16 times greater than the weight of the hemostatic structure, shape stability was superior and fluid absorption properties of high level were maintained even after the pressure was applied, showing a high fluid retention capacity.

In the case of comparative example 1, the shape collapsed immediately upon absorption of 0.9% saline solution, and in the case of comparative example 2, the shape stability was so poor that it was impossible to measure fluid absorption and retention itself. In the case of comparative example 3, as 0.9% saline solution was absorbed, gels were formed, and when the pressure was applied to measure fluid retention, shape maintenance failed, making it impossible to measure fluid retention.

Experimental Example

Evaluation of Shape Stability after Immersing and Shaking

Figure 2:
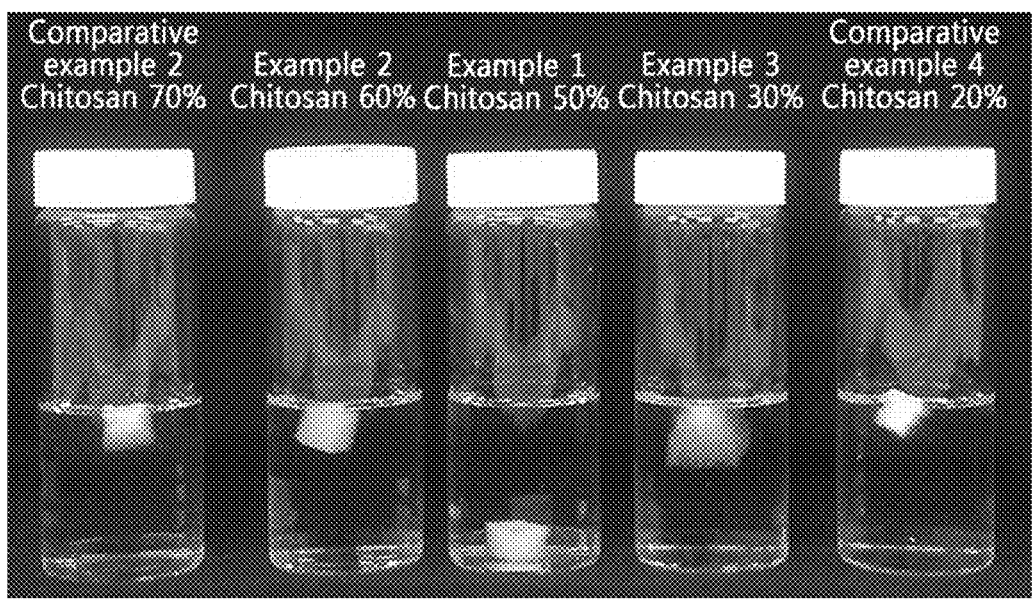
FIG. 2 is a photographic image showing the results when one minute passed after porous structures of examples 1-3 and comparative examples 2 and 4 were immersed in distilled water.
Figure 3:
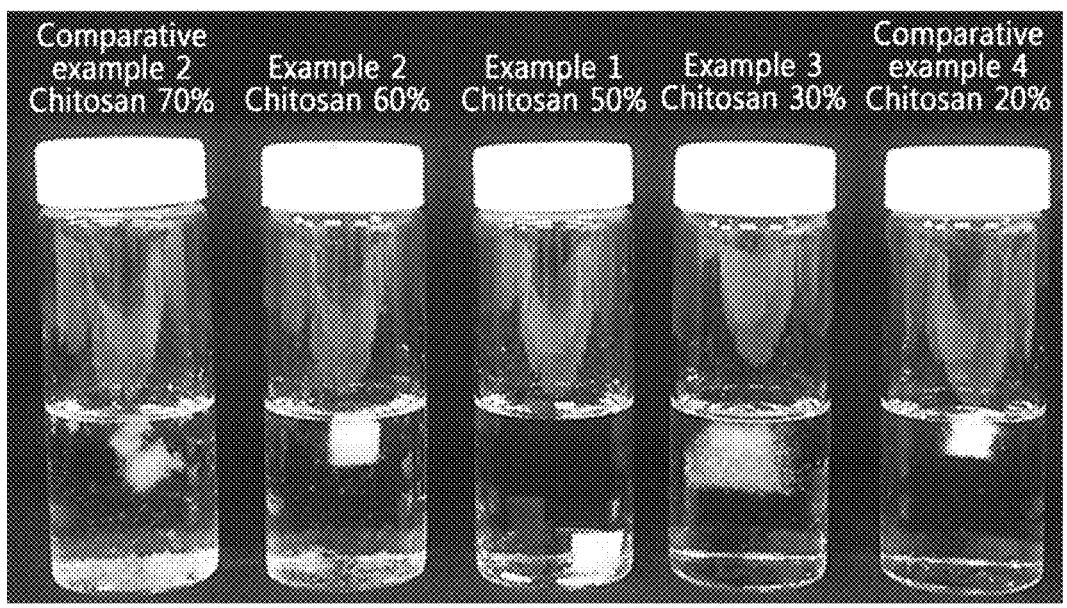
FIG. 3 is a photographic image showing the results after porous structures of examples 1-3 and comparative examples 2 and 4 were immersed in distilled water and shaken at 60 cycles per minute for 5 minutes.

The porous structures of examples 1 to 3 and comparative examples 2 and 4 were cut into pieces of dimensions 1 cm×1 cm×1 cm (width×length×height), and, and results when 1 minute passed after immersing in distilled water of 25☐ and results after shaking at 60 cycles per minute for 5 minutes are shown in FIGS. 2 and 3, respectively.

In the case of examples 1 to 3 having a weight ratio of water-soluble chitosan and sodium carboxymethyl cellulose of from 65:35 to 25:75, the rate of fluid absorption was fast and shape maintaining properties were superior even after shaking. In contrast, in the case of comparative example 2 having a 70:30 weight ratio of water-soluble chitosan and sodium carboxymethyl cellulose, after immersing, the rate of distilled water absorption was very slow as compared to the example samples, and after shaking, the foam shape collapsed rapidly and shape stability was very poor. In the case of comparative example 4 having a 20:80 weight ratio of water-soluble chitosan and sodium carboxymethyl cellulose, when immersing in distilled water, gelation occurred on the surface of the porous structure, and even after shaking for 5 minutes, distilled water did not permeate into the porous structure by a gel blocking phenomenon.

Experimental Example

Observation of Pore Structure on Surface and in Cross Section

The pore structures on the surface and in cross section of the porous structures prepared in examples 1 and 3 and comparative examples 1 to 3 were observed through scanning electron microscope (SEM) photographic images.

Each porous structure sample was frozen in liquid nitrogen, cut in cross section, and coated with gold for 150 seconds using an ion coater (E-1045), and the surface and cross section were observed under 50-time magnification using field emission scanning electron microscope (FE-SEM, SU 8010). The observation is shown in the following FIG. 13.

Figure 13:
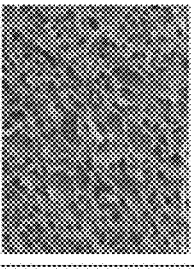
FIG. 13 is surface and cross-sectional photographic images of a porous structure of examples 1 and 3 and comparative examples 1, 2 and 3 observed using field emission scanning electron microscope (FE-SEM, SU 8010).

Referring to the above FIG. 13, all showed a porous structure in cross section, but in the case of comparative example 1 using water-soluble chitosan alone and comparative example 2 containing water-soluble chitosan in excess, many closed pores on the surface were observed. In contrast, in the case of examples 1 and 3, they were found to have a good porous structure on the surface and in cross section, and accordingly, it is expected that blood absorption will be favorable to them.

Experimental Example

Evaluation of Blood Absorption Rate

The blood absorption rate was evaluated using the porous structures prepared in example and comparative example and current commercial hemostatic dressing products in Table 2 (comparative examples 5-8).

TABLE 2

| | Brand name | Manufacturer | Key ingredient |
|---|---|---|---|
| Comparative example 5 | SURGICEL | ETHICON | Oxidized regenerated cellulose |
| Comparative example 6 | QuikClot | Combat Medical Systems | Clay mineral (Kaolin) attached on gauze |
| Comparative example 7 | CELOX RAPID | Medtrade Products | Chitosan powder attached on gauze |
| Comparative example 8 | HemCon Bandage | Hemcon Inc. | Chitosan foam |

The blood absorption rate was evaluated by measuring the time required for 100 μl of blood (blood taken from dogs) to be completed absorbed by a hemostatic porous structure of dimensions 1 cm×1 cm×1 cm (width×length×height) after the blood is dripped into the hemostatic porous structure, and from this, it was intended to evaluate suitability as hemostatic dressings. In the case of commercial hemostatic dressing products of comparative examples 5 to 9, one layer was used as in the shape of the products and measured in dimensions of 1 cm×1 cm (width×length).

The blood absorption rate results and photographic images before and after blood absorption are shown in the following FIG. 14. The photographic image after absorption is a photographic image after blood was dripped and completely absorbed. In the case of comparative examples 3 and 8, blood was not absorbed even after 30 minutes passed, so the photographic image is one after 30 minutes passed.

Referring to FIG. 14, comparative example 1 using water-soluble chitosan alone took 14 seconds to completely absorb blood and dissolution of parts contacted with blood was observed. In the case of comparative example 3 using sodium carboxymethyl cellulose alone, parts contacted with blood formed gels, leading to a gel blocking phenomenon that prevented blood from being absorbed into the inside, so blood was not absorbed even after 30 minutes passed.

On the other hand, examples 1, 3, and 7 and comparative example 2 using water-soluble chitosan and sodium carboxymethyl cellulose showed rapid blood absorption properties within a few seconds, and particularly, example 1 having a 50:50 weight ratio of water-soluble chitosan and sodium carboxymethyl cellulose and example 7 containing calcium ions, they absorbed blood immediately upon contact with the blood. Among commercial products, comparative example 5 (Surgicel), comparative example 6 (QuikClot), and comparative example 7 (Celox Rapid) products absorbed blood immediately upon contact with the blood, while chitosan foam-type comparative example 8 (Hemcon Bandage) did not completely absorb blood even after 30 minutes passed. Accordingly, the porous hemostatic agent according to the embodiment of the present disclosure had absorption properties that are similar or superior to commercial hemostatic products.

Experimental Example

Evaluation of Blood Coagulation Properties—Coagulation Time 10 Minutes

The blood coagulation properties were evaluated using the porous structures prepared in examples 1 to 6 and comparative examples 1 to 4, current commercial hemostatic dressing products in Table 2 (comparative examples 5-8), a collagen product coated with human fibrinogen and human thrombin Baxter TachoSil (comparative example 9), a cotton gauze (comparative example 10), and blood alone (comparative example 11).

For the blood coagulation properties, in the case of the porous structures prepared in example and comparative example, 100 μl of a mixed solution of blood and an anticoagulant (sodium citrate, 3.8 w/v %) at a 9:1 volume ratio was dripped into sample of dimensions 1 cm×1 cm×1 cm (width×length×height) and coagulated in a 37° C. incubator for 10 minutes with the addition of 10 μl of 0.2M $CaCl_2$ aqueous solution, and blood not having participated in coagulation was eluted in 12.5 mL of distilled water again. 200 μl of the eluate was taken and measured to determine absorbance [AB] at 540 nm wavelength, and 200 μl of the distilled water was measured to determine absorbance [AW] at 540 nm wavelength, and to obviate the influence of distilled water included in the blood eluate on absorbance, absorbance of the hemostatic material was calculated by the following equation.

Absorbance for evaluation of blood coagulation properties=Absorbance of blood eluate [AB]−Absorbance of distilled water [AW]

In the case of commercial hemostatic dressing products of comparative examples 5 to 10, one layer was used as in the shape of the products and measured in dimensions of 1 cm×1 cm (width×length). In the case of comparative example 11, absorbance was measured using blood alone without any hemostatic dressing by the same method as above. Photographic images of the evaluated results and absorbance are shown in the following FIG. 15 and FIGS. 4 and 5 respectively.

Figure 4:
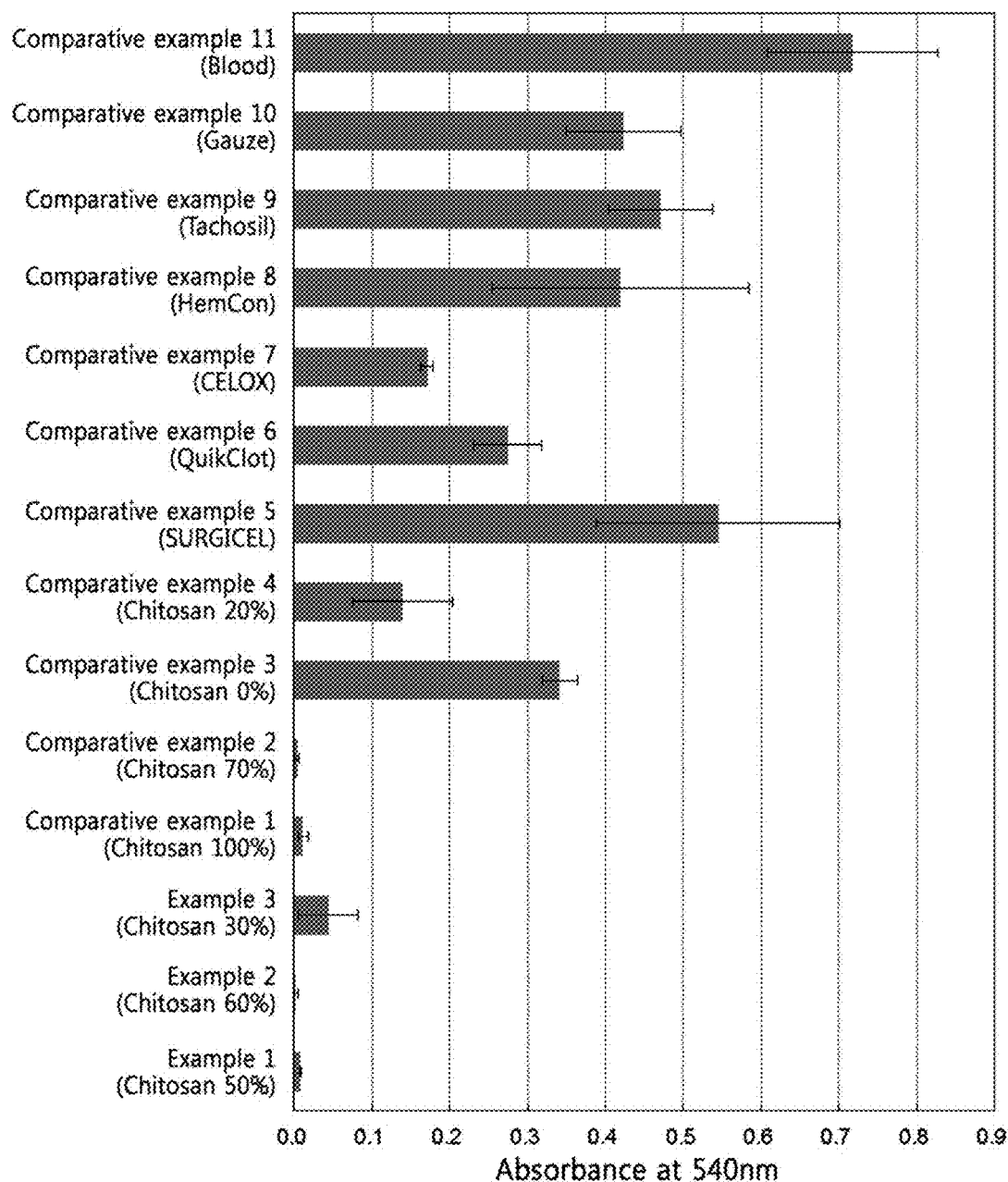
FIG. 4 is a graph showing the results of evaluating blood coagulation properties using porous structures according to examples 1-3 and comparative examples 1-4, commercial hemostatic agents of comparative examples 5-10, and blood alone (comparative example 11).
Figure 15:
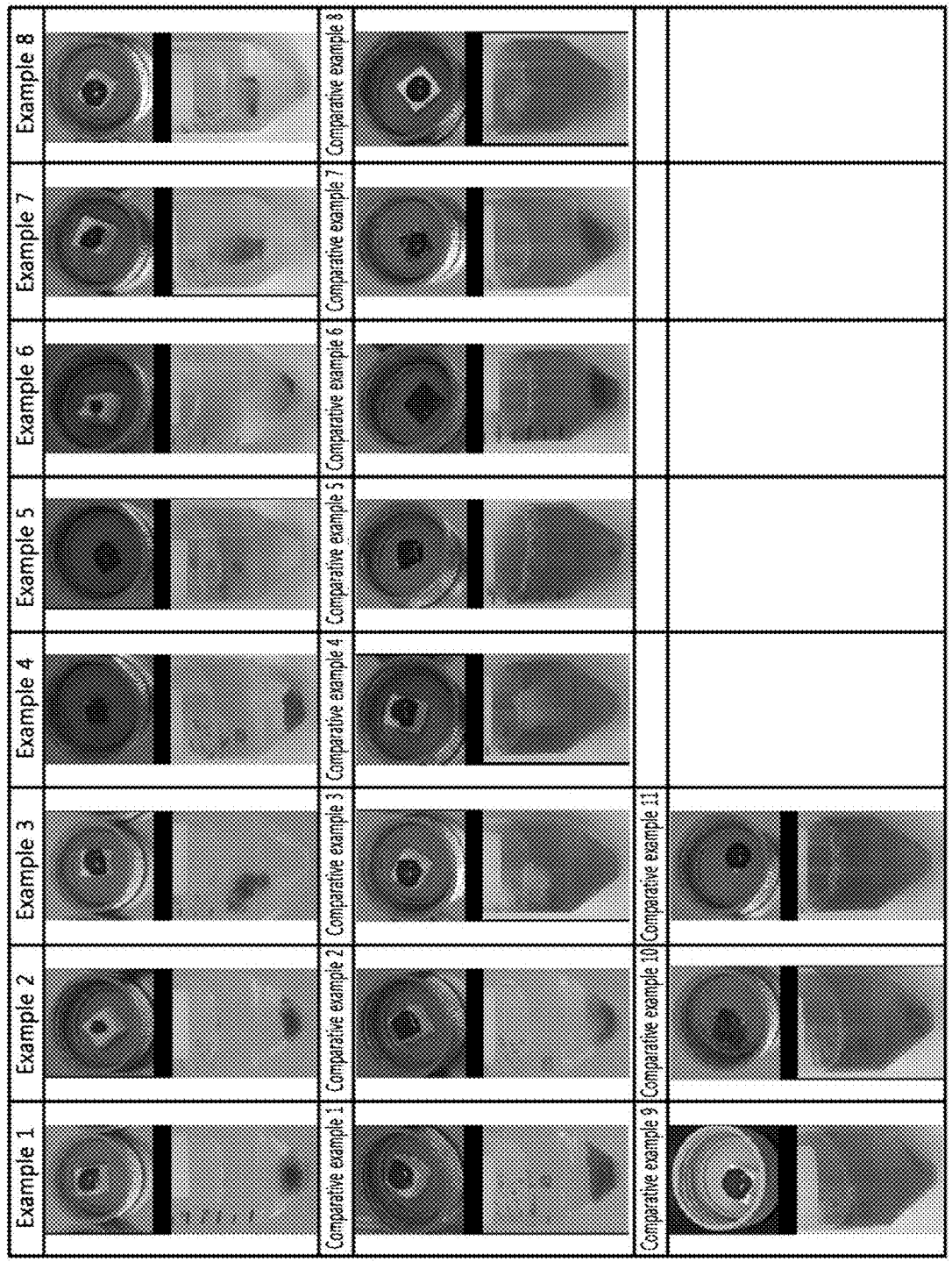
FIG. 15 is photographic images of the evaluated results and absorbance.

Referring to FIG. 15 and FIG. 4, it was identified that the porous structures of examples 1 to 3 had a smaller amount of blood that does not coagulate and is left as compared to existing products of comparative examples 5 to 10, and thus had very low absorbance of the blood eluate and outstanding blood coagulation properties.

In the case of comparative examples 1 and 2 containing a large amount of water-soluble chitosan, the blood coagulation properties were good, but when they come into contact with blood, dissolution occurred and shape stability significantly reduced.

In the case of comparative example 1 made from water-soluble chitosan alone, the chitosan structure collapsed immediately upon contact with blood, and in the case of comparative example 2 containing water-soluble chitosan in excess, when contacted with blood, shape stability significantly reduced and a loosening phenomenon occurred. On the other hand, comparative example 3 using sodium carboxymethyl cellulose alone and comparative example 4 containing a small amount of chitosan showed a similar level to commercial products, but had so much poorer blood coagulation properties than examples 1 to 3.

Figure 5:
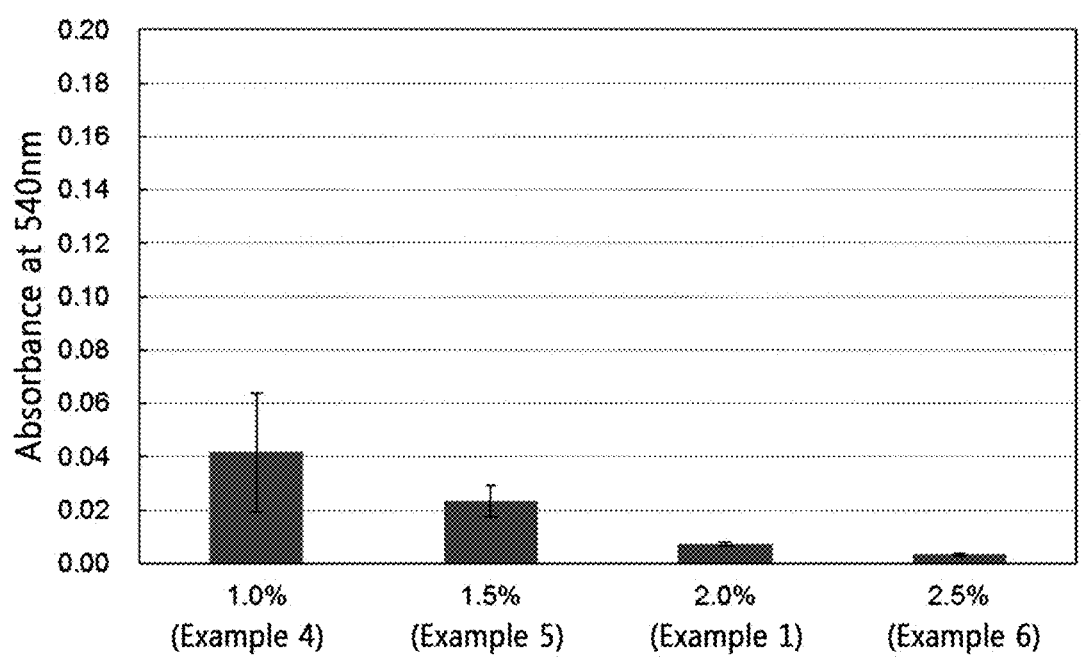
FIG. 5 is a graph showing the results of evaluating blood coagulation properties of porous structures of example 1 and examples 4-6.

Furthermore, the porous structures of example 1 and examples 4 to 6 prepared at varying concentration of the composition used for freeze-drying with the same 50:50 weight ratio of water-soluble chitosan and sodium carboxymethyl cellulose were evaluated to identify the blood coagulation properties, and its results are shown in FIG. 5.

Referring to FIG. 5, when a weight ratio of water-soluble chitosan and sodium carboxymethyl cellulose is 50:50, absorbance was very low regardless of the concentration of water-soluble chitosan and sodium carboxymethyl cellulose used for freeze-drying, and thus the hemostatic properties were found superior. On the other hand, it was identified that with the increasing concentration of water-soluble chitosan and sodium carboxymethyl cellulose used for freeze-drying, the blood coagulation properties were gradually getting better. It seems that as the concentration of the composition used to prepare the porous structure increases, higher content of chitosan and sodium carboxymethyl cellulose that can react with blood is present in the prepared porous structure and the coagulation properties are getting better.

Experimental Example

Blood Coagulation Rate

The blood coagulation properties as a function of coagulation time, namely, blood coagulation rate was evaluated using the porous structures prepared from examples 1 and 3, commercial products of comparative examples 5 to 7 and blood alone (comparative example 11).

The blood coagulation rate was evaluated by measuring absorbance of the blood eluate by the same method as described in "Experimental example: Evaluation of blood coagulation properties—coagulation time 10 minutes" except samples subjected to coagulation in a 37□ incubator for the blood coagulation time of 1, 2, 3, 5 and 10 minutes were used. In the case of comparative example 11, absorbance was measured using blood alone without any hemostatic dressing by the same method as above. Its evaluated results are shown in the following FIG. 6.

Figure 6:
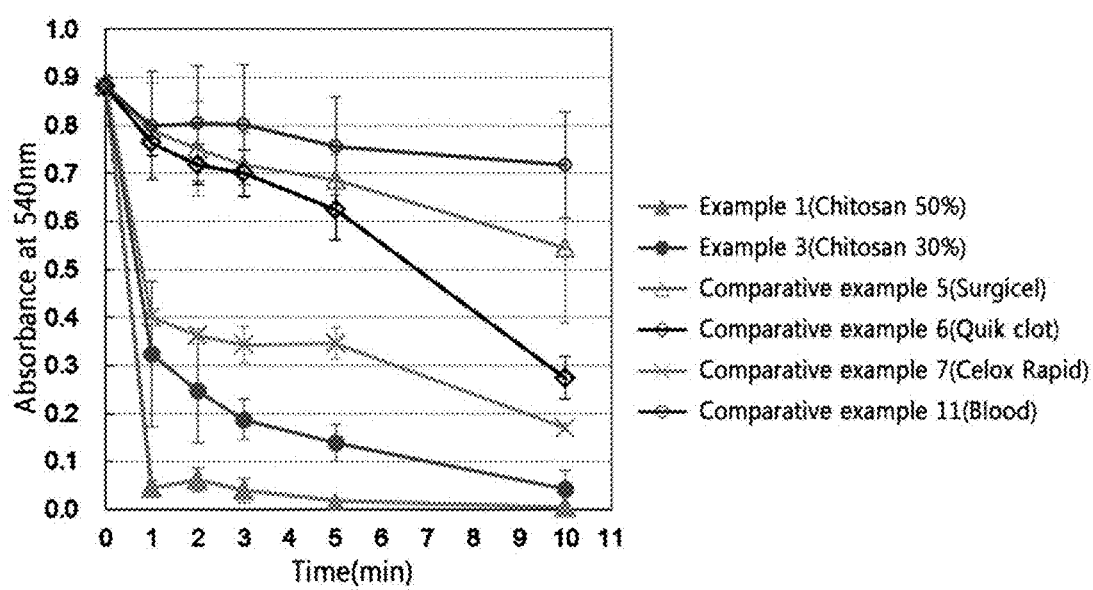
FIG. 6 is a graph showing evaluation of blood coagulation properties at varying coagulation time using porous structures of examples 1 and 3 and commercial hemostatic agents of comparative examples 5-7, and blood alone (comparative example 11).

Referring to FIG. 6, in the case of example 1 and example 3 including water-soluble chitosan and sodium carboxymethyl cellulose, blood coagulation usually occurred within 1 minute and absorbance was 0.25 or less within 2 minutes. Particularly, in the case of example 1, it was identified that blood coagulation finished within 1 minute. Among commercial products of comparative examples, in the case of comparative example 7 (CELOX RAPID), blood coagulation occurred over considerate portions within 1 minute, but absorbance was 0.30 or above in 5 minutes after the start of coagulation. Particularly, in the case of comparative examples 6 and 7, the blood coagulation rate had a very low value.

Experimental Example

Observation of Blood Coagulation Behavior

The blood coagulation behaviors of the porous structures prepared in examples 1 and 3 and comparative examples 1 to 3 were observed.

200 µl of a mixed solution of blood and an anticoagulant (sodium citrate, 3.8 w/v %) at a volume ratio of 9:1 was dripped into the porous structures of dimensions 1 cm×1 cm×1 cm (width×length×height), and coagulated in a 37° C. incubator for 10 minutes with the addition of 20 µl of 0.2M $CaCl_2$ aqueous solution. Subsequently, fixation with 2% formaldehyde solution in PBS (phosphate-buffered saline) for 2 hours was followed by washing with a mixed solution of water and ethanol at a gradually increasing ratio of ethanol (10:0, 8:2, 5:5, 2:8, 0:10), and drying. Each of the dried samples were coated with gold for 150 seconds using an ion coater (E-1045) and observed under 6,000-time magnification using field emission scanning electron microscope (FE-SEM, SU 8010), and the observation is shown in FIG. 16.

Figure 16:
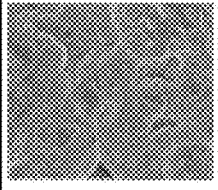
FIG. 16 is blood coagulation behavior photographic images of porous structures of examples 1 and 3 and comparative examples 1 to 3 observed under 6,000-time magnification using field emission scanning electron microscope (FE-SEM, SU 8010).

Referring to FIG. 16, in the case of comparative example 3, red blood cells not involved in clot formation were obviously found on the surface, and it was identified that as the content of water-soluble chitosan increases, a thicker clot layer was formed on the surface and coated red blood cells. Particularly, in the case of examples 1 and 3, fibrin fibers surrounding red blood cells were clearly observed.

Experimental Example

Influence of Calcium Ion Introduction

Figure 7:
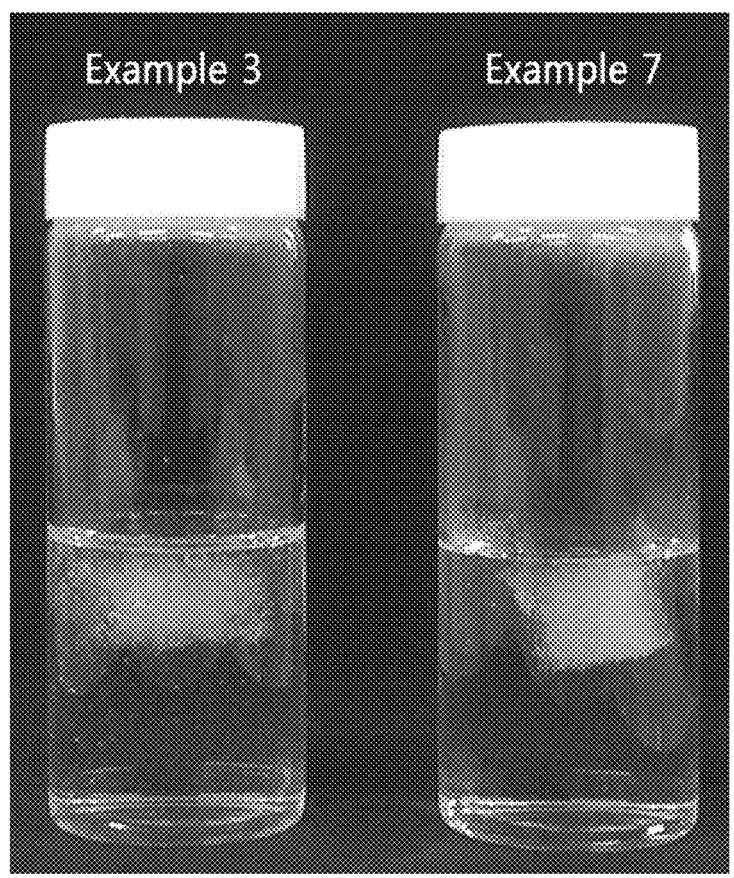
FIG. 7 is a photographic image showing evaluation of shape sustaining properties after porous structures of example 3 and example 7 were immersed in distilled water and shaken at 60 cycles per minute.

After the porous structures prepared in example 3 and example 7 were cut into pieces of dimensions 1 cm×1 cm×1 cm (width×length×height), immersed in distilled water, and shaken at 25° C. for 5 minutes at 60 cycles per minute, the shape maintaining properties were evaluated, and its results are shown in FIG. 7.

Referring to FIG. 7, it was identified that as compared to example 3, in the case of example 7, the shape maintaining capacity further improved and the rate of fluid absorption became fast. This is because, in the case of example 7, cross-linking between carboxymethyl cellulose chains not having participated in ionic bonding with water-soluble chitosan is induced by calcium ions to form a network, thereby further increasing shape stability. Furthermore, in the absence of calcium ion treatment, a gel blocking phenomenon occurs a bit, resulting in low absorption rate, while in the presence of calcium ion treatment, calcium divalent ions form bonds with carboxyl groups of carboxymethyl cellulose, resulting in reductions in gel blocking phenomenon and fast fluid absorption. Furthermore, in the case of example 7, calcium is released when contacted with blood, and it is expected to further promote blood coagulation.

Figure 8:
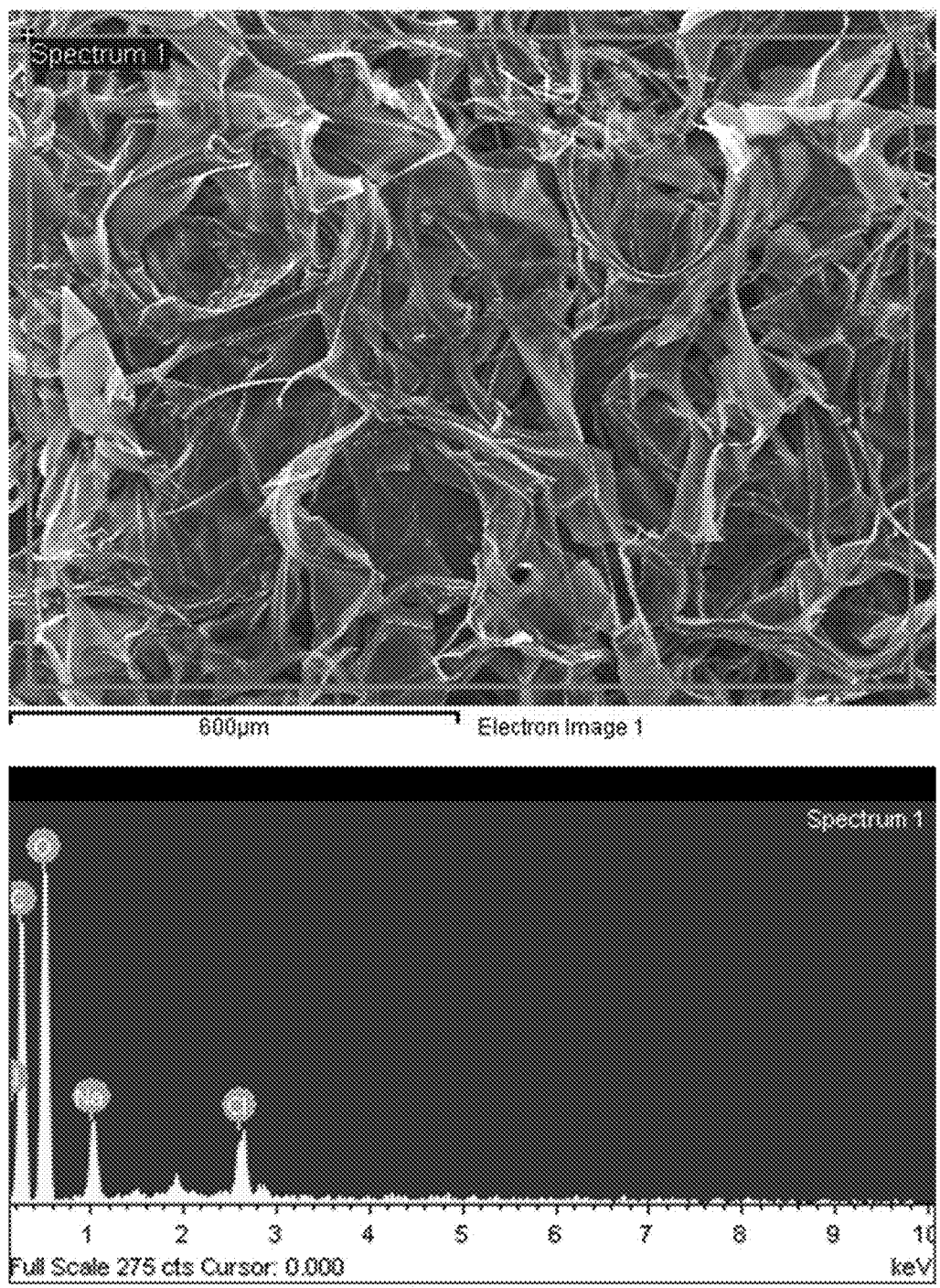
FIG. 8 is a cross-sectional photographic image of a porous structure of example 3 observed using field emission scanning electron microscope (FE-SEM, SU 8010) and an image showing elemental analysis based on EDX measurements made five times repeatedly.
Figure 9:
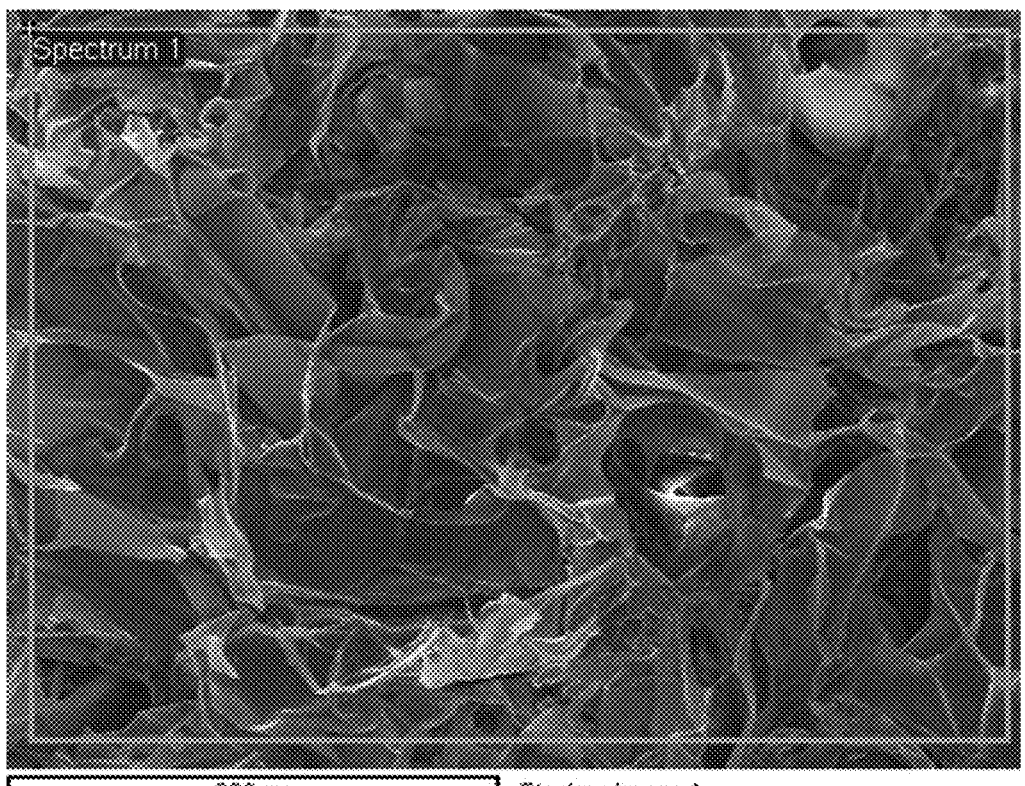
FIG. 9 is a cross-sectional photographic image of a porous structure of example 7 observed using field emission scanning electron microscope (FE-SEM, SU 8010) and an image showing elemental analysis based on EDX measurements made five times repeatedly.
Figure 9:
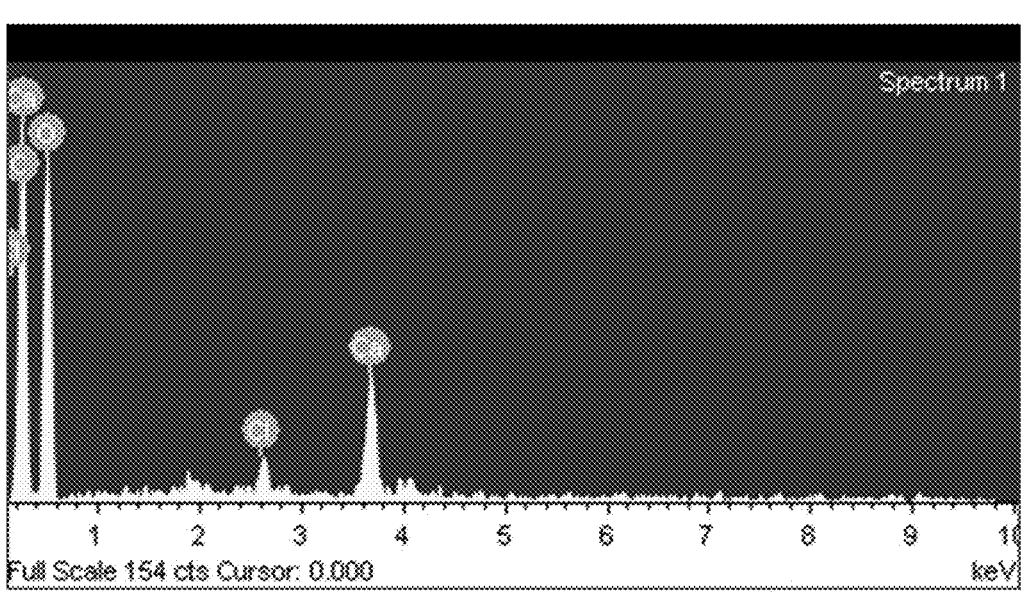

The porous structures of example 3 and example 7 were coated with gold for 150 seconds using an ion coater (E-1045), and images obtained by SEM observation of the cross section using field emission scanning electron microscope (FE-SEM, SU 8010), and 5 repeated EDX measurements and elemental analysis are shown in each of FIG. 8 (example 3) and FIG. 9 (example 7).

In the case of example 3 (FIG. 8), Na atoms were detected from sodium carboxymethyl cellulose used in preparation and were detected in 4.13% in weight percentage, and Ca atoms were not detected. In the case of example 7 (FIG. 9), Na atoms were not detected, and Ca atoms were detected due to calcium treatment and were detected in 4.58% in weight percentage. From this, it could be seen that Ca ions were effectively introduced.

Referring to FIGS. 8 and 9, a porous structure is present even after calcium treatment in the same way as before treatment, making fast blood absorption very advantageous, and calcium was released quickly through a wide surface area, and thus it is thought that it will be effective to promote blood coagulation.

For the porous structures prepared in examples 7 and 8, the blood coagulation properties was evaluated by the same method as "Experimental example: Evaluation of blood coagulation properties—Coagulation time 10 minutes" and evaluation of blood coagulation properties of "Experimental example: Blood coagulation rate" described above, and its results are shown in FIGS. 10 and 11.

Figure 10:
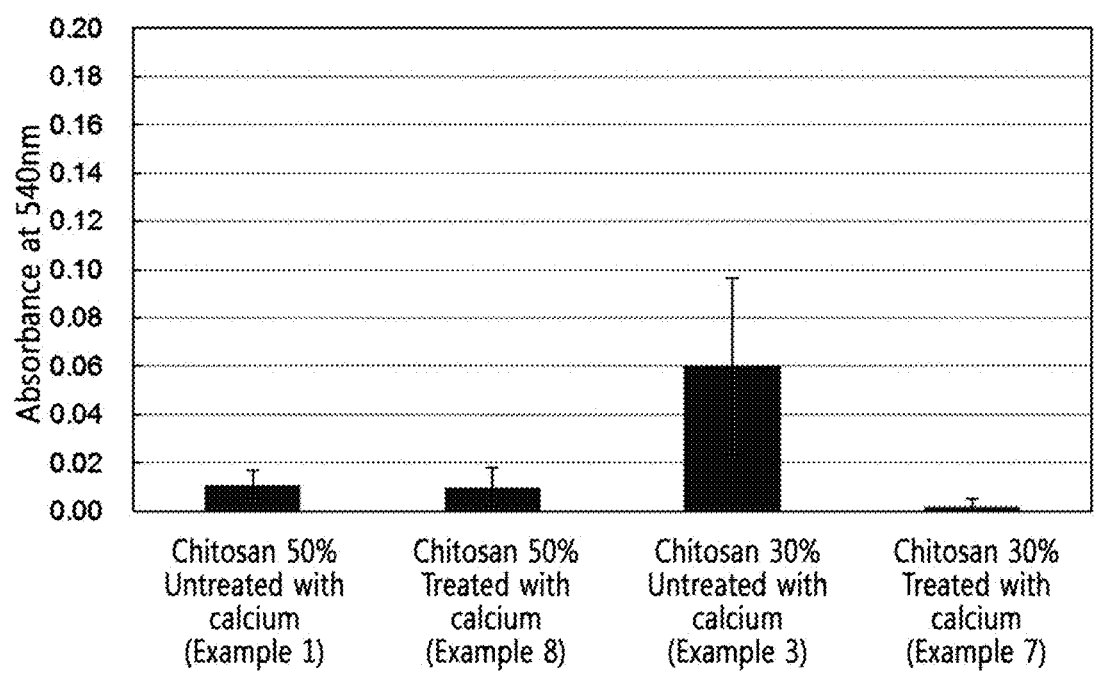
FIG. 10 is a graph showing the results of evaluating blood coagulation properties using porous structures according to examples 1, 3, 7 and 8.

Referring to FIG. 10, in the case of example 1 and example 8 in which the content of water-soluble chitosan and the content of carboxymethyl cellulose compound is 50:50, absorbance was found very low regardless of calcium ion introduction. In contrast, when comparing example 3 and example 7 in which the content of water-soluble chitosan and the content of carboxymethyl cellulose compound is 30:70, absorbance of the two samples was 0.2 or less and thus blood coagulation properties were outstanding, but in the case of example 7 having introduced calcium ions, absorbance significantly reduced, and from this, it was identified that blood coagulation properties were further improved by calcium ion introduction.

Figure 11:
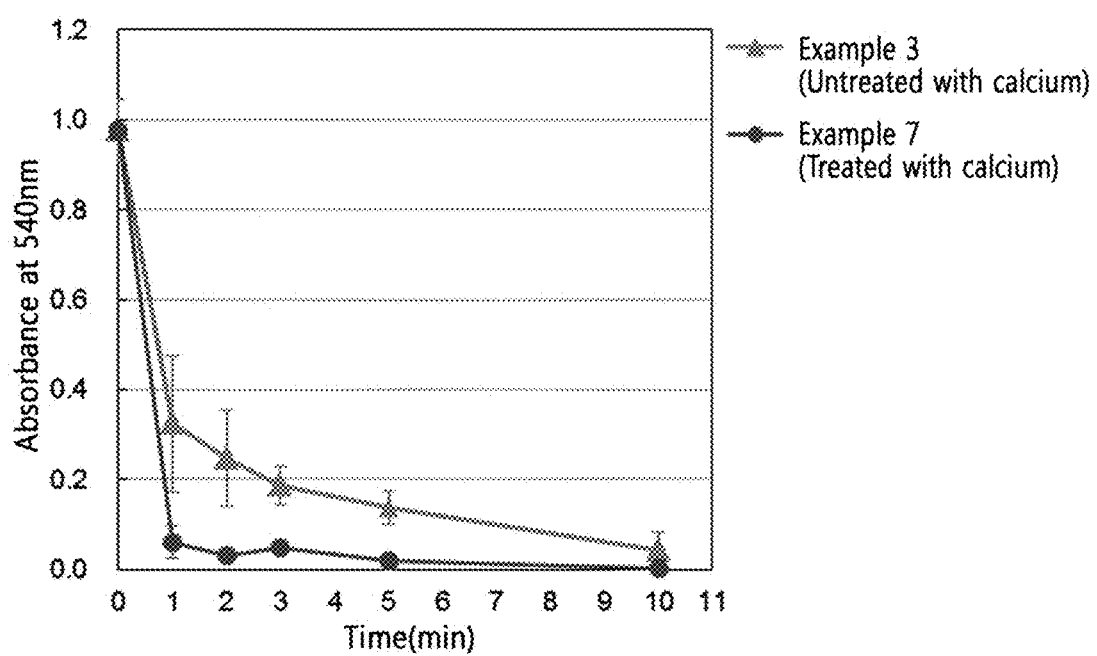
FIG. 11 is a graph showing evaluation of blood coagulation properties at varying coagulation time using porous structures of examples 3 and 7.

Referring to FIG. 11 showing blood coagulation rates, when comparing example 3 and example 7 in which the content of water-soluble chitosan and the content of carboxymethyl cellulose compound is 30:70, it was identified that in the case of example 7 having introduced calcium ions, the blood coagulation rate also became fast greatly and thus blood coagulation occurred within 1 minute.

Experimental Example

Observation of Hemostatic Effect

Figure 12A:
FIGS. 12a and 12b are photographic images respectively showing the hemostatic effect and clotting results using a porous structure of example 1.
Figure 12B:

The hemostatic effect of example 1 was observed using rats as an excessive bleeding animal model. After a wound of 3 mm was made in the arteria femoralis in the lengthwise direction of the rat, causing bleeding for 30 seconds, the porous structure of example 1 was placed on the wound, and observed after applying a force of 200 gf for 1 minute. It was identified that in the case of general gauzes, bleeding did not stop and continued, while in the case of being treated with the porous structure of example 1, bleeding from the wound site stopped within 3 minutes, and after the porous structure was removed, clots were formed fast. As a result of evaluating how much blood was absorbed by measuring the weight of the porous structure before and after hemostasis, the weight of the porous structure before blood absorption was 0.115 g, and the weight of the porous structure having absorbed blood after completion of hemostasis evaluation was 1.793 g, so an amount of blood absorption to the weight before blood absorption was 14.59 g/g, showing high fluid absorption properties. The photographic images of hemostatic effect and clot formation results are shown in FIGS. 12a and 12b, respectively.

What is claimed is:

1. A porous structure comprising:
   water-soluble chitosan having a surface thereof with —$NH_3^+$ positive charge; and
   a carboxymethyl cellulose-based compound,
   wherein the carboxymethyl cellulose-based compound is bonded with calcium ions, and a weight ratio of the water-soluble chitosan and the carboxymethyl cellulose-based compound is from 50:50 to 25:75,
   wherein a degree of deacetylation of the water-soluble chitosan is from 80 to 100%.

2. The porous structure according to claim 1, wherein a content of the calcium ions is 0.2 to 10 parts by weight per 100 parts by weight of the water-soluble chitosan and the carboxymethyl cellulose-based compound.

3. The porous structure according to claim 1, wherein the porous structure has a blood absorption rate of 15 seconds or less, and the blood absorption rate is the time required for 100 μl of blood to be completely absorbed by a hemostatic porous material of dimensions 1 cm×1 cm×1 cm (width× length×height) after the blood was dripped into the hemostatic porous material.

4. The porous structure according to claim 1, wherein the porous structure has absorbance of 0.30 or less in evaluating blood coagulation properties, and
   the evaluation of blood coagulation properties is conducted by dripping 100 μl of blood mixed with an anticoagulant (sodium citrate, 3.8 w/v %) at a volume ratio of 9:1 into a porous structure of dimensions 1 cm×1 cm×1 cm (width×length×height), inducing coagulation in a 37° C. incubator for 10 minutes with the addition of 10 μl of 0.2M CaCl2 aqueous solution, allowing some of the blood that did not participate in coagulation to be eluted in 12.5 mL of distilled water again, taking 200 μl of the eluate, measuring absorbance [AB] at 540 nm wavelength, measuring absorbance [AW] of 200 μl of distilled water at 540 nm wavelength, and performing a calculation using the following equation to obviate the influence of distilled water included in the blood eluate on absorbance:

Absorbance for evaluation of blood coagulation properties=Absorbance of blood eluate [$AB$]– Absorbance of distilled water [$AW$].

5. The porous structure according to claim 1, wherein the porous structure further comprises at least one of an active ingredient, a plasticizer, an antimicrobial material, a hemostatic material, a cell, an enzyme, an antigen, and a pigment.

6. The porous structure according to claim 1, wherein the porous structure is of foam type.

* * * * *